United States Patent
Van Atta

[11] Patent Number: 6,093,301
[45] Date of Patent: Jul. 25, 2000

[54] SLAB GEL CASSETTES WITH SIDE OPENINGS

[75] Inventor: Daniel L. Van Atta, Clayton, Calif.

[73] Assignee: Bio-Rad Laboratories, Inc., Hercules, Calif.

[21] Appl. No.: 09/151,895

[22] Filed: Sep. 11, 1998

[51] Int. Cl.[7] .................................................. G01N 27/26
[52] U.S. Cl. .......................................... 204/617; 204/616
[58] Field of Search .................................... 204/616, 618, 204/615, 617, 619, 620; 425/117, 436 R; 249/117

[56] References Cited

U.S. PATENT DOCUMENTS

| | | | |
|---|---|---|---|
| 5,304,292 | 4/1994 | Jacobs et al. | 204/619 |
| 5,632,877 | 5/1997 | Van Atta | 204/618 |
| 5,685,967 | 11/1997 | Manis et al. | 204/616 |

OTHER PUBLICATIONS

Pp. 9–12 of the instruction booklet for the NuPage Electrophoresis System—Bis–Tris Gels, Sep. 1999.

*Primary Examiner*—Jill Warden
*Assistant Examiner*—Alex Noguerola
*Attorney, Agent, or Firm*—Townsend and Townsend and Crew LLP

[57] ABSTRACT

A slab gel cassette for slab electrophoresis with a side opening or slot for the bottom edge of the gel is improved by directing the foot of the gel space (i.e., the lower edge of the space that turns toward the side opening) at an obtuse angle (greater than 120°) relative to the remainder of the slab rather than the 90° angle of the prior art. The gel can be flattened for drying without cutting off the foot. A further improvement is the placement of notches in the side edges of the cassette opposite the ends of the slot, and a still further improvement is the placement of additional notches in the ends of the slot itself opposite the aforementioned notches.

6 Claims, 6 Drawing Sheets

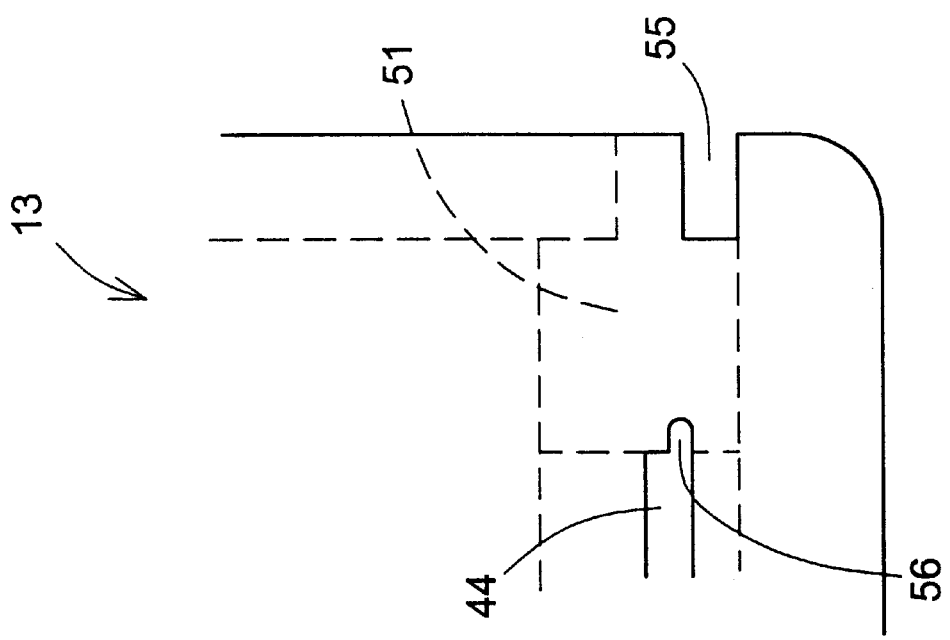

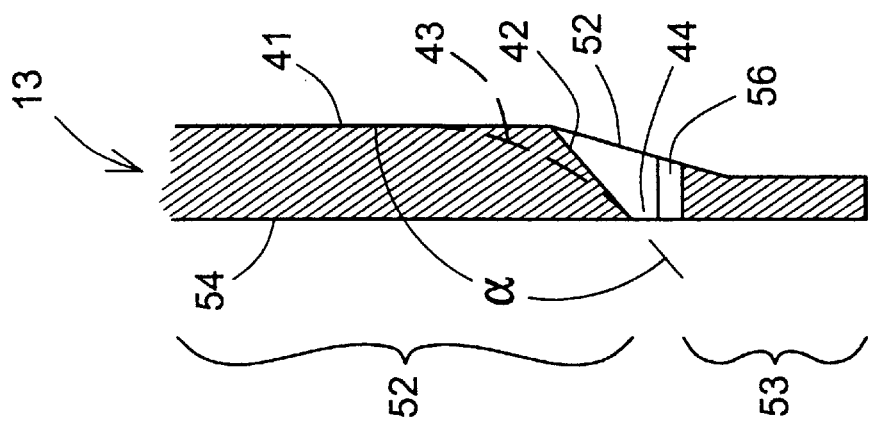
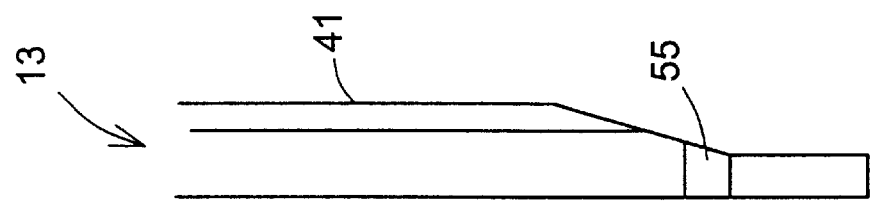
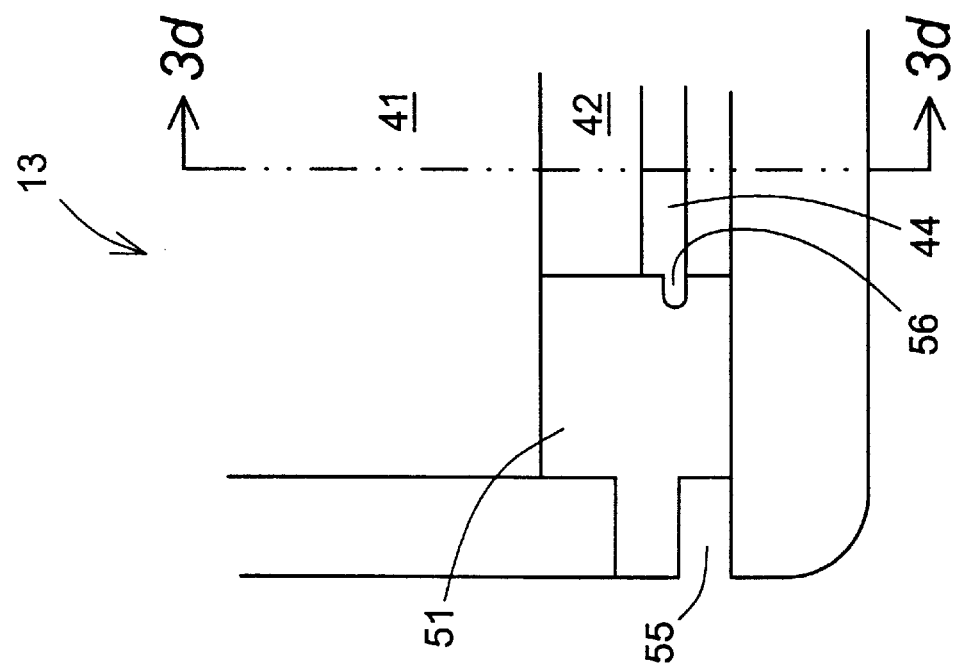
*Fig. 3d*
*Fig. 3c*
*Fig. 3b*

SLAB GEL CASSETTES WITH SIDE OPENINGS

BACKGROUND OF THE INVENTION

Electrophoresis in slab-shaped gels is a common analytical technique in biotechnical laboratories, since a slab gel offers many beneficial features to the analytical chemist or biochemist. Included among these are the ability to divide the gel into several lanes and perform separate analyses in the various lanes under identical conditions, the ease of removing the gel from its enclosure and staining it to permit visualization of the bands, and the ease of scanning the gel and recording the results to identify and quantify the contents of each band. Slab gels are commonly held in cassettes, which are parallel plate enclosures that have a gap of precise width between the plates to define the gel thickness. The typical cassette is designed to permit the loading of samples along the top edge of the gel while exposing both the top and bottom edges of the gel to permit contact with upper and lower electrode buffers, respectively, when the cassette is placed in an electrophoresis cell. The gel is prepared in the cassette itself by filling the space between the plates with a solution of gel-forming monomer or prepolymer and allowing the solution to polymerize.

Casting the gel in this manner requires that the bottom edge of the gel space be temporarily sealed off in a manner that results in a gel with a cleanly defined bottom edge and yet allows the user to remove the seal without tearing or otherwise damaging the bottom edge of the gel. This is accomplished with a strip of flexible adhesive-backed tape. While the tape holds the gel liquid adequately and can be removed without tearing the gel, experience has shown that simply applying the tape across the two bottom edges of the two plates does not produce the most well defined gel boundaries. The two plates are welded together along their side edges, and the sealing tape must seal not only against the parallel bottom edges but also against the weld line which continues to the ends of the bottom edges. Also, the two bottom edges provide very little surface area for the tape to seal against.

These problems have been addressed in the prior art by designing the gel cassette so that the gel space makes a 90° turn at the bottom. Thus, instead of a gel space opening at the very bottom of the cassette (with the two plates in a vertical orientation), the cassette has a gel space that passes through one of the two parallel plates and opens at the side of the cassette through a slot in one of the plates. No weld lines intersect with the slot, and the surface area surrounding the slot is planar and continuous since it is part of the broad face of the plate. Since the surrounding surface is considerably wider than the edge surfaces, this arrangement provides a greater surface area to which the tape can be sealed. Once the gel is cast and the electrophoretic separation has been completed, the two plates are broken away from each other along the slot to allow the gel to be lifted out for staining, drying or other electrophoretic processes. This is facilitated by using a wide hand tool in a stepped area along the two side edges and the bottom edge of the gel plates.

A gel formed in a cassette of this type therefore has a "foot" along its bottom edge, i.e., a lip projecting from the rest of the gel at a 90° angle. The foot thus passes through a side opening or slot in the cassette that is coplanar with one of the plates and places the bottom edge of the gel flush with the outer surface of the plate. Once electrophoresis has been performed and the plates are split apart to expose the gel, the slot remains intact in one of the two pieces of the cassette, with the foot inside the slot. To extract the gel without damaging it, the foot must be pushed out through the slot. This is a delicate and difficult procedure that is prone to error and entails a risk of breaking the gel. In addition, once the gel is fully removed, the foot must be cut off before the gel can be dried, since the gel is dried in a flattened condition and the sharp right angle of the foot and the added thickness at the 90° outer corner prevents the foot from being flattened. Pushing the gel through the slot and cutting off the foot both add to the time required to perform an electrophoretic analysis in a slab gel, and both provide opportunities for operator error.

SUMMARY OF THE INVENTION

The disadvantages of slab gel cassettes that form a gel with a foot along its bottom edge are addressed by the present invention, which resides in a cassette that, while still containing a side seal for the bottom edge of the gel space, does so by orienting the strip along the bottom edge at an obtuse angle relative to the remainder of the gel. The profile of the gel space, i.e., its cross section in the vertical plane perpendicular to the two support plates, will thus have a center line that passes through a slot in one of the plates at an obtuse angle relative to the center line in the flat portion of the gel space. The 90° corner of the gel space in prior art cassettes is thus replaced either by a smooth curve or by a corner that is less sharp than 90°, thereby reducing the gel thickness at the corner. This results in a gel with a thickness that is constant or more closely approximates a constant thickness all the way to the bottom edge of the gel, and makes it possible for one to lay the entire gel flat without removing the foot.

A further improvement in the cassette design is a notch on the outer side edge of the cassette substantially opposing the end of the slot (i.e., substantially co-linear with the slot), and preferably one on each of the two outer side edges substantially opposing the two ends of the slot. These notches facilitate the breaking apart of the plates along the slot, thereby opening the slot when the plates are separated and avoiding the need to push the gel through the slot. In particularly preferred embodiments, the cassette also includes an additional pair of notches, one at each of the two ends of the slot, each of these inner notches opposing one of the two outer notches in the side edges of the plate. This further ensures that the separation of the plates will occur along the slot, fully exposing the entire gel including the gel foot.

These and other objects, features and advantages of the invention will become more clear from the description that follows.

BRIEF DESCRIPTION OF THE DRAWINGS

FIG. 2d is a cross section taken along the line 2d—2d of FIG. 2a.

FIG. 3a is a plan view of one side of one lower corner of the back plate of FIG. 1.

FIG. 3b is a plan view of the other side of the same corner of the back plate.

FIG. 3c is an end view of the same corner of the back plate.

FIG. 3d is a cross section taken along the line 3d—3d of FIG. 3a.

DETAILED DESCRIPTION OF THE INVENTION AND PREFERRED EMBODIMENTS

While this invention can be implemented and embodied in a variety of ways, the common features that characterize the invention can best be understood by a detailed study of one particular structure within the scope of the invention. The following description is such a study and is intended to be illustrative only, without limiting the scope of the invention.

Figure 1:
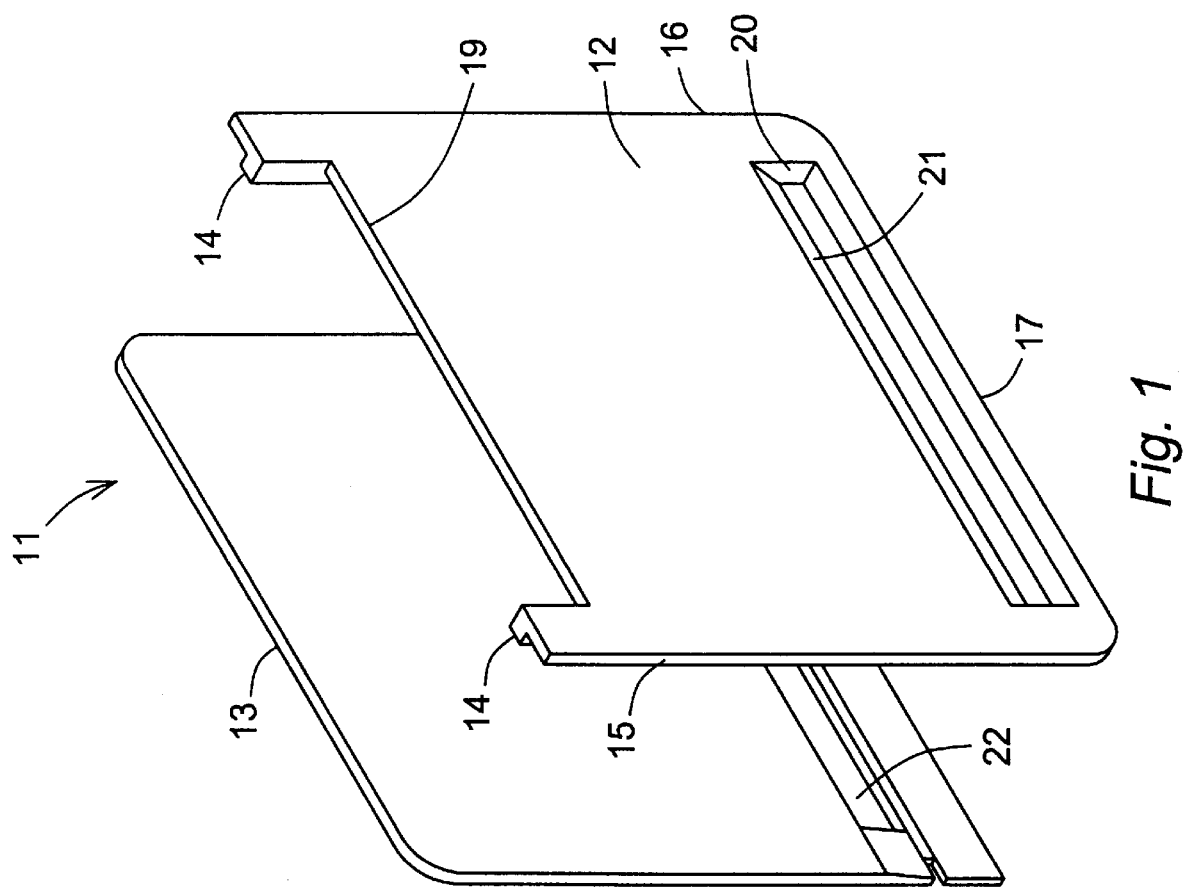
FIG. 1 is a perspective view of the front and back plates of a slab gel cassette in accordance with the present invention.

The gel cassette 11 is shown in a perspective view in FIG. 1. The two parallel plates of the cassette are a front plate 12 and a back plate 13. The plates are shown separated, but in use are welded together along a raised ridge 14 that runs adjacent to the side edges 15, 16 and bottom edge 17 of one plate. The raised ridge 14 establishes a gap between the opposing surfaces of the plates, which serves as the gel space. Along the top edge of the front plate 12 is a rectangular cutout or open space 19. This serves as an opening to facilitate the insertion of a "comb" into the upper edge of the gel space before the gel has solidified. When the comb is removed from the solidified gel, the teeth of the comb leave a row of wells along the upper edge of the gel to hold samples that are to be separated by electrophoresis in the gel. The cutout 19 together with the opposing wall of the back plate 13 also serve as a means to contain an upper electrode buffer solution and to place the solution in contact with the upper edge of the gel, when the cassette is placed in an electrophoretic cell designed for this type of cassette. The higher back plate 13 forms one wall of a chamber for the buffer solution while the cell in which the cassette is inserted provides the remaining walls, the chamber extending through the cutout 19 in the top edge of the front plate. This is a common construction for electrophoresis cells, one example of which is illustrated in U.S. Pat. No. 5,632,877.

Along the bottom edge 17 of the front plate 12 is an indentation 20 with a slanted upper surface or ceiling 21 whose opposite side (not visible in this view) protrudes from the plate surface to form one wall of the angled foot of the invention. The opposing wall of the foot, at the same angle, is formed by a slanted indentation 22 in the inner wall of the back plate 13. These features are more clearly visible in the subsequent figures.

Figure 2A:
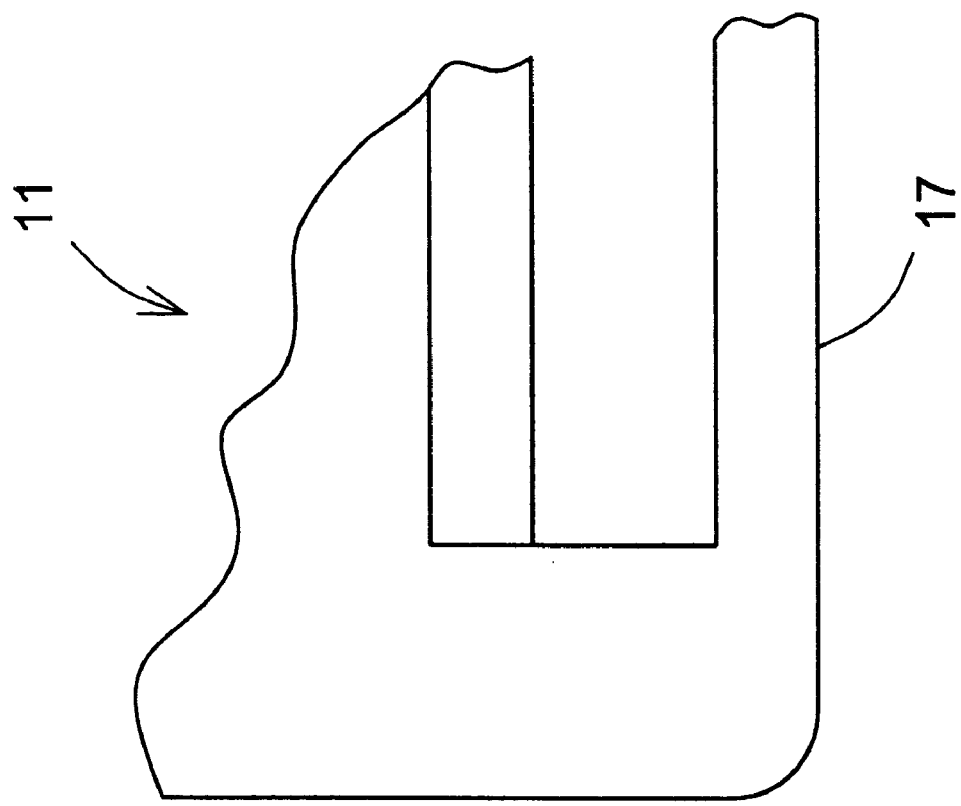
FIG. 2a is a plan view of one side of one lower corner of the front plate of FIG. 1.
Figure 2D:
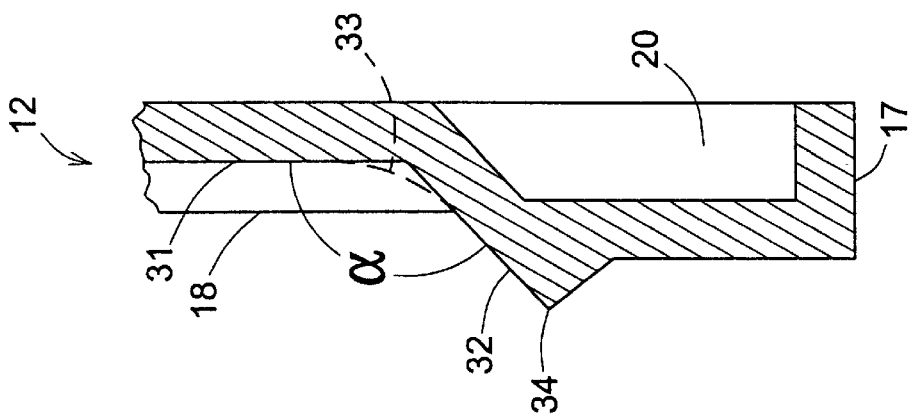
Figure 2C:
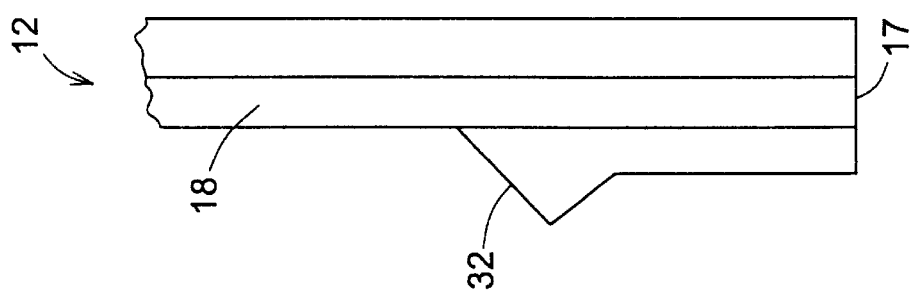
FIG. 2c is an end view of the same corner of the front plate.
Figure 2B:
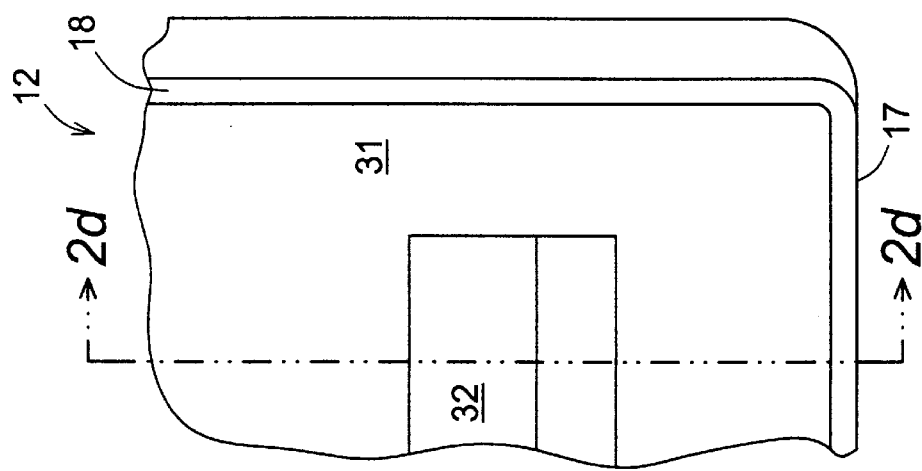
FIG. 2b is a plan view of the other side of the same corner of the front plate.

The area adjacent to the bottom edge 17 of the front plate 12 is shown in FIGS. 2a through 2d. FIG. 2a is an outer plan view of one lower corner of the front plate, i.e., a plan view of the side that faces outward when the two plates are welded together, while FIG. 2b is a inner plan view, i.e., a view of the side that faces the back plate. FIG. 2c is an end view of the same corner, while FIG. 2d is a cross section taken along the line 2d—2d of FIG. 2b.

The inwardly directed face 31 of the front plate adjoins an angled surface 32 that forms one wall of the angled section of the gel space (i.e., the angled foot). The angle α at the juncture of the two surfaces is at least about 120°, preferably between about 120° and about 175°, more preferably between about 130° and about 160°, and most preferably about 135°. The junction of the two surfaces is shown in this embodiment as a sharp angle, the two surfaces each being flat. Alternatively, the junction of the two surfaces may be replaced by a continuous curve as shown by the dashed line 33. The back of the angled surface 32 is the indentation 20 shown in FIG. 1. The lower edge 34 of the angled surface 32 protrudes to form a bead that runs along the bottom and both sides of the plate. The two plates are welded along this bead and along other surfaces.

FIGS. 3a through 3d show the bottom edge of the back plate 13. FIG. 3a is an outer plan view of one lower corner of the back plate (the side facing outward when the two plates are welded together), FIG. 3b is an inner plan view, FIG. 3c is an end view, and FIG. 3d is a cross section taken along the line 3d—3d of FIG. 3b.

Figure 4:
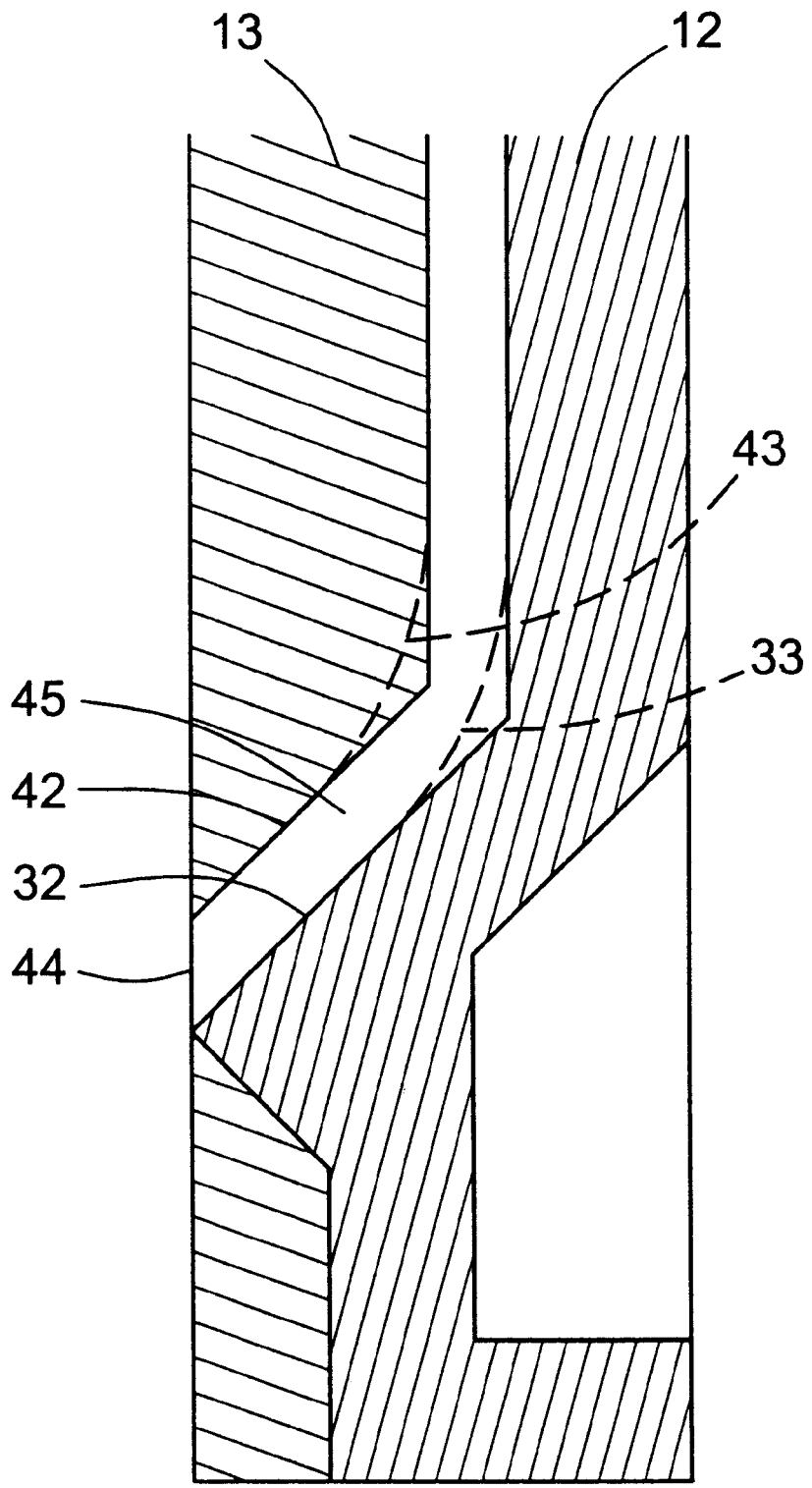
FIG. 4 is a cross section view of the front and back plate welded together to form the completed cassette.

The inwardly directed face 41 of the back plate is flat and adjoins an angled surface 42 at the same angle α as the adjoining surfaces in the front plate. Here as well, the junction line of the two surfaces can be replaced by a smooth curve (dashed line 43) terminating at the same angle. The lower edge of the angled surface 42 forms the boundary of the slot mentioned above, which is an elongated opening 44 in the plate exposing the lower edge of the gel. The front and back plates are shown together in cross section in FIG. 4. The gap 45 between the angled surfaces 32, 42 is the portion of the gel space that forms the angled foot.

Returning to FIG. 3b, the slot 44 terminates at its end in a wall portion 51 (the corresponding wall portion 52 at the opposite end of the slot is visible in FIG. 3d; the two ends are mirror images of each other since the plates are symmetrical about their center lines). As can be seen in FIG. 3d, the wall portions 51, 52 are slanted on their outer faces to bridge the two portions of the back plate above and below the slot 44, the upper portion 52 being thicker than the lower portion 53. The inner face 54 of the back plate however is entirely planar, and the portion of this inner face that forms the back of the wall portion 51 forming the end of the slot is likewise coplanar with the remainder of the inner face. The result is a continuous flat planar surface surrounding the inner face side of the slot 44. This provides a broad flat planar area with no intersecting weld lines, an area to which a sealing tape can be easily adhered to seal the slot while the gel is being cast.

Breakage of the upper portion of the back plate to permit removal of the gel is facilitated by notches 55 along the side edges of the back plate (only one is visible in the drawing but a mirror image notch is present on the opposite side edge), the notches being substantially co-linear (approximately level) with the slot 44. Additional internal notches 56 (again only one is visible but a mirror image notch is present at the opposite side) further facilitate the break. The internal notches are at each end of the slot 44 are likewise substantially co-linear (approximately level) with the external notches 55, the internal and external notches being at opposite edges of the wall portions 51, 52 at each end of the slot.

The terms "substantially co-linear" and "approximately level" are intended to denote that the center line of the notch may in fact be co-linear with the center line of the slot (i.e., at an equal distance from the bottom edge of the plate) or the two may deviate slightly from co-linearity. The same is true for the inner notches and outer notches. The notches and slot may thus have upper or lower boundaries that are co-linear (as shown in FIG. 3a, 3b and 3d in which the lower boundaries of the slot and the inner notch are co-linear), or the upper boundary of one may be co-linear with the lower boundary of the other (as shown in the same Figures in which the upper boundary of the outer slot is co-linear with the lower boundary of the inner slot), or any combination or arrangement in between. The intent is that the slot and notches are close enough to being level with each other to promote a straight break.

While the slot 44 is shown in the front plate 12 (the plate with the cutout 19 along its top edge), alternative constructions may place the slot in the back plate 13. In a further alternative, the plates can be formed such that the angled foot section of the gel space is formed entirely in one plate. The front plate in this embodiment would not contain a slanting surface 32 extending into the back plate; instead, this surface would be part of the back plate.

Still further variations and modifications, all within the scope of the invention, will be readily apparent to those skilled in the art.

What is claimed is:

1. In a cassette for retaining a slab gel to be used as an electrophoretic separation medium, said cassette formed of two parallel plates joined together with a gap therebetween to define a slab-shaped gel space that has upper and lower exposed edges so that a gel retained in said gel space can be placed in contact with upper and lower electrode buffers, said plates being shaped such that said gel space is planar except for a strip adjacent to said lower exposed edge which is nonplanar relative to the remainder of said gel space whereby said lower exposed edge is in the plane of an outer face of one of said plates, wherein the improvement is that strip forms an obtuse angle of at least about 120° with the remainder of said gel space.

2. A cassette in accordance with claim 1 in which said obtuse angle is from about 120° to about 175°.

3. A cassette in accordance with claim 1 in which said obtuse angle is from about 130° to about 160°.

4. In a cassette for retaining a slab gel to be used as an electrophoretic separation medium, said cassette formed of first and second parallel plates joined together with a gap therebetween to define a slab-shaped gel space that has upper and lower exposed edges so that a gel retained in said gel space can be placed in contact with upper and lower electrode buffers, said first and second plates being shaped such that said gel space is planar except for a strip adjacent to said lower exposed edge, said strip being nonplanar relative to the remainder of said gel space such that said lower exposed edge is defined by a slot in said first plate, the improvement comprising a first notch in an outer edge of said first plate at a location substantially opposing an end of said slot.

5. A cassette in accordance with claim 4 comprising a second notch located so that the first and second notches are in opposing outer edges of said first plate at locations substantially opposing both ends of said slot.

6. A cassette in accordance with claim 4 comprising a second outer notch located so that the first and second notches are in opposing outer edges of said first plate at locations substantially opposing both ends of said slot, and two inner notches inside said slot, one at each end of said slot at a location substantially opposing one of said outer notches.

* * * * *